US012558065B2

(12) United States Patent
Iguchi

(10) Patent No.: US 12,558,065 B2
(45) Date of Patent: Feb. 24, 2026

(54) ULTRASOUND TRANSDUCER

(71) Applicant: TERUMO KABUSHIKI KAISHA, Tokyo (JP)

(72) Inventor: Akira Iguchi, Mishima (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 451 days.

(21) Appl. No.: 17/484,809

(22) Filed: Sep. 24, 2021

(65) Prior Publication Data

US 2022/0008039 A1 Jan. 13, 2022

Related U.S. Application Data

(63) Continuation of application No. PCT/JP2020/012778, filed on Mar. 23, 2020.

(30) Foreign Application Priority Data

Mar. 26, 2019 (JP) ................................. 2019-058608

(51) Int. Cl.
| | |
|---|---|
| *A61B 8/00* | (2006.01) |
| *A61B 8/02* | (2006.01) |
| *A61B 8/12* | (2006.01) |
| *B06B 1/06* | (2006.01) |

(52) U.S. Cl.
CPC .............. *A61B 8/4494* (2013.01); *A61B 8/12* (2013.01); *B06B 1/067* (2013.01); *B06B 2201/76* (2013.01)

(58) Field of Classification Search
CPC ......... A61B 8/4494; A61B 8/12; A61B 8/445; B06B 1/067; B06B 1/0648; B06B 1/0662; B06B 2201/76
See application file for complete search history.

(56) References Cited

U.S. PATENT DOCUMENTS

| | | | |
|---|---|---|---|
| 5,327,895 A | 7/1994 | Hashimoto et al. | |
| 5,377,682 A | 1/1995 | Ueno et al. | |
| | (Continued) | | |

FOREIGN PATENT DOCUMENTS

| | | |
|---|---|---|
| CN | 108336216 A | 7/2018 |
| JP | H08191835 A | 7/1996 |
| | (Continued) | |

OTHER PUBLICATIONS

Office Action (The First Office Action) issued Mar. 1, 2023, by the National Intellectual Property Administration, P. R. China in corresponding Chinese Patent Application No. 202080014073.X and an English translation of the Office Action. (11 pages).

(Continued)

*Primary Examiner* — Pascal M Bui Pho
*Assistant Examiner* — Neshat Baset
(74) *Attorney, Agent, or Firm* — Buchanan Ingersoll & Rooney PC

(57) ABSTRACT

An ultrasound transducer according to the disclosure includes: a piezoelectric element; and a support member that supports the piezoelectric element, in which: the piezoelectric element includes a flat piezoelectric body, a first electrode that is laminated on at least one side of the piezoelectric body in a thickness direction, and a second electrode that is laminated on at least the other side of the piezoelectric body in the thickness direction; the support member includes a first terminal that is connected to the first electrode of the piezoelectric element, and a second terminal that is connected to the second electrode of the piezoelectric element; and the first terminal and the second terminal respectively include portions that do not overlap the piezoelectric element in the thickness direction.

17 Claims, 8 Drawing Sheets

(56) References Cited

U.S. PATENT DOCUMENTS

| | | | |
|---|---|---|---|
| 5,503,145 A | 4/1996 | Clough | |
| 7,327,072 B2 | 2/2008 | Fujimura et al. | |
| 7,969,068 B2 | 6/2011 | Yokobori et al. | |
| 2006/0025691 A1 | 2/2006 | Tanaka et al. | |
| 2007/0216257 A1* | 9/2007 | Fujimura | G10K 11/30 |
| | | | 310/326 |
| 2009/0160293 A1* | 6/2009 | Yokobori | B06B 1/0688 |
| | | | 29/25.35 |
| 2010/0066207 A1 | 3/2010 | Saito | |
| 2012/0143063 A1* | 6/2012 | Robinson | A61B 8/145 |
| | | | 600/472 |
| 2015/0042210 A1 | 2/2015 | Nagareda et al. | |
| 2015/0045671 A1* | 2/2015 | Ozawa | B06B 1/064 |
| | | | 600/459 |
| 2016/0346808 A1* | 12/2016 | Miyazawa | B06B 1/0644 |
| 2018/0204997 A1 | 7/2018 | Ohashi | |
| 2019/0117200 A1* | 4/2019 | Morimoto | A61B 8/12 |

FOREIGN PATENT DOCUMENTS

| | | | |
|---|---|---|---|
| JP | 2006198425 A | 8/2006 | |
| JP | 2009152785 A | 7/2009 | |
| JP | 2009152786 A | 7/2009 | |
| JP | 2009153603 A | 7/2009 | |
| JP | 2009206789 A | 9/2009 | |
| WO | 2008/056611 A1 | 5/2008 | |

OTHER PUBLICATIONS

The extended European Search Report issued Mar. 22, 2022, by the European Patent Office in corresponding European Patent Application No. 20776445.7-1001. (8 pages).

Office Action (Notice of Reasons for Refusal) issued Sep. 26, 2023, by the Japan Patent Office in corresponding Japanese Patent Application No. 2021-509403 and an English translation of the Office Action. (6 pages).

International Search Report (PCT/ISA/210) with translation and Written Opinion (PCT/ISA/237) mailed on Apr. 14, 2020, by the Japan Patent Office as the International Searching Authority for International Application No. PCT/JP2020/012778.

English Translations of the International Search Report (Form PCT/ISA/210) and the Written Opinion of the International Searching Authority (Form PCT/ISA/237) issued Apr. 14, 2020, by the Japan Patent Office in corresponding International Application No. PCT/JP2020/012778. (6 pages).

* cited by examiner

ULTRASOUND TRANSDUCER

CROSS-REFERENCES TO RELATED APPLICATIONS

This application is a continuation of International Application No. PCT/JP2020/012778 filed on Mar. 23, 2020, which claims priority to Japanese Patent Application No. 2019-058608 filed on Mar. 26, 2019, the entire content of both of which is incorporated herein by reference.

FIELD OF THE DISCLOSURE

The disclosure generally relates to an ultrasound transducer.

BACKGROUND DISCUSSION

An ultrasound probe including an ultrasound transducer is used as a transmitter and receiver of ultrasound in a medical ultrasound diagnostic apparatus. An ultrasound diagnosis can be performed in a state where an ultrasound probe is loaded into a catheter, and the catheter is inserted into a body.

Japanese Patent Application Publication No. 2006-198425 A discloses an ultrasound probe including an active transducer element having a top main surface and a bottom main surface, a top electrode that is formed on the top main surface, a bottom electrode that is formed on the bottom main surface, a conductive backing element that covers the bottom electrode, a first lead that is electrically connected to the top electrode, and a second lead that is electrically connected to the conductive backing element.

A demand for downsizing an ultrasound probe to be loaded into a catheter is important to reduce patient burden and to enhance the insertability to a body-cavity having a smaller diameter, such as a deep blood vessel.

The downsizing of the ultrasound probe can be implemented by downsizing an ultrasound transducer including a piezoelectric element that includes piezoelectric body and a pair of electrodes. However, when the ultrasound transducer is downsized, the piezoelectric element also becomes relatively small. Therefore, the electrodes in the piezoelectric element are also relatively small, so that work of connecting an electric signal line that connects the piezoelectric element to an external power supply to the electrode of the piezoelectric element becomes rather difficult.

SUMMARY

An ultrasound transducer is disclosed, which has a configuration that achieves a rather easy connection of an electric signal line to a piezoelectric element.

An ultrasound transducer as a first aspect of the disclosure includes: a piezoelectric element; and a support member that supports the piezoelectric element, in which: the piezoelectric element includes a flat piezoelectric body, a first electrode that is laminated on at least one side of the piezoelectric body in a thickness direction, and a second electrode that is laminated on at least the other side of the piezoelectric body in the thickness direction; the support member includes a first terminal that is connected to the first electrode of the piezoelectric element, and a second terminal that is connected to the second electrode of the piezoelectric element; and the first terminal and the second terminal respectively include portions that do not overlap the piezoelectric element in the thickness direction.

In one embodiment of the disclosure, the support member includes a support main body portion that is laminated on the piezoelectric element at the other side in the thickness direction, and extends externally further than the piezoelectric element in a direction orthogonal to the thickness direction, and the first terminal and the second terminal are supported by the support main body portion.

In another embodiment of the disclosure, the first electrode of the piezoelectric element includes a surface electrode layer that is positioned at the one side in the thickness direction of the piezoelectric body, a rear surface electrode layer that is positioned at the other side in the thickness direction of the piezoelectric body, and an interlock conductive portion that interlocks the surface electrode layer and the rear surface electrode layer to each other.

In one embodiment of the disclosure, the first terminal is connected to the rear surface electrode layer of the first electrode between the piezoelectric element and the support main body portion.

In another embodiment of the disclosure, the second terminal is connected to the second electrode between the piezoelectric element and the support main body portion.

In one embodiment of the disclosure, the piezoelectric element includes a first portion including a portion overlapping the first terminal and a portion overlapping the second terminal, in the thickness direction, and a second portion excluding the first portion, and a whole region at the other side in the thickness direction of the second portion is covered by the support main body portion.

In accordance with an aspect, an ultrasound transducer comprising: a piezoelectric element, the piezoelectric element includes a piezoelectric body, a first electrode that is laminated on at least one side of the piezoelectric body in a thickness direction, and a second electrode that is laminated on at least the other side of the piezoelectric body in the thickness direction; a support member, the support member includes a first terminal that is connected to the first electrode of the piezoelectric element, and a second terminal that is connected to the second electrode of the piezoelectric element; the first terminal and the second terminal respectively include portions that do not overlap the piezoelectric element in the thickness direction; electrical signal lines connected to the first electrode and the second electrode; and wherein the support body includes a support main body, the support main body having a pair of grooves configured to receive the electrical signal lines connected to the first electrode and the second electrode, two pairs of grooves being sectioned on a top surface of the support main body portion opposed to a surface of the piezoelectric element.

In accordance with another aspect, a diagnostic imaging apparatus, the diagnostic imaging apparatus comprising: a diagnostic imaging catheter, the diagnostic imaging catheter including an insertion portion and an operation portion, the insertion portion includes an ultrasound probe and a sheath, the ultrasound probe comprising: a piezoelectric element, the piezoelectric element includes a flat piezoelectric body, a first electrode that is laminated on at least one side of the piezoelectric body in a thickness direction, and a second electrode that is laminated on at least the other side of the piezoelectric body in the thickness direction; a support member, the support member includes a first terminal that is connected to the first electrode of the piezoelectric element, and a second terminal that is connected to the second electrode of the piezoelectric element; the first terminal and the second terminal respectively include portions that do not overlap the piezoelectric element in the thickness direction; and electrical signal lines connected to the first electrode and the second electrode; and an external device configured to be mechanically and electrically connected to the diagnostic imaging catheter through a hub, and wherein the electric signal lines of the ultrasound probe extend from the ultrasound probe to a connector portion of the hub, and wherein the connector portion of the hub is configured to electrically connect the ultrasound probe and the external device to each other.

According to the disclosure, an ultrasound transducer is disclosed that has a configuration that achieves a rather easy connection of an electric signal line to a piezoelectric element.

DETAILED DESCRIPTION

Figure 1:
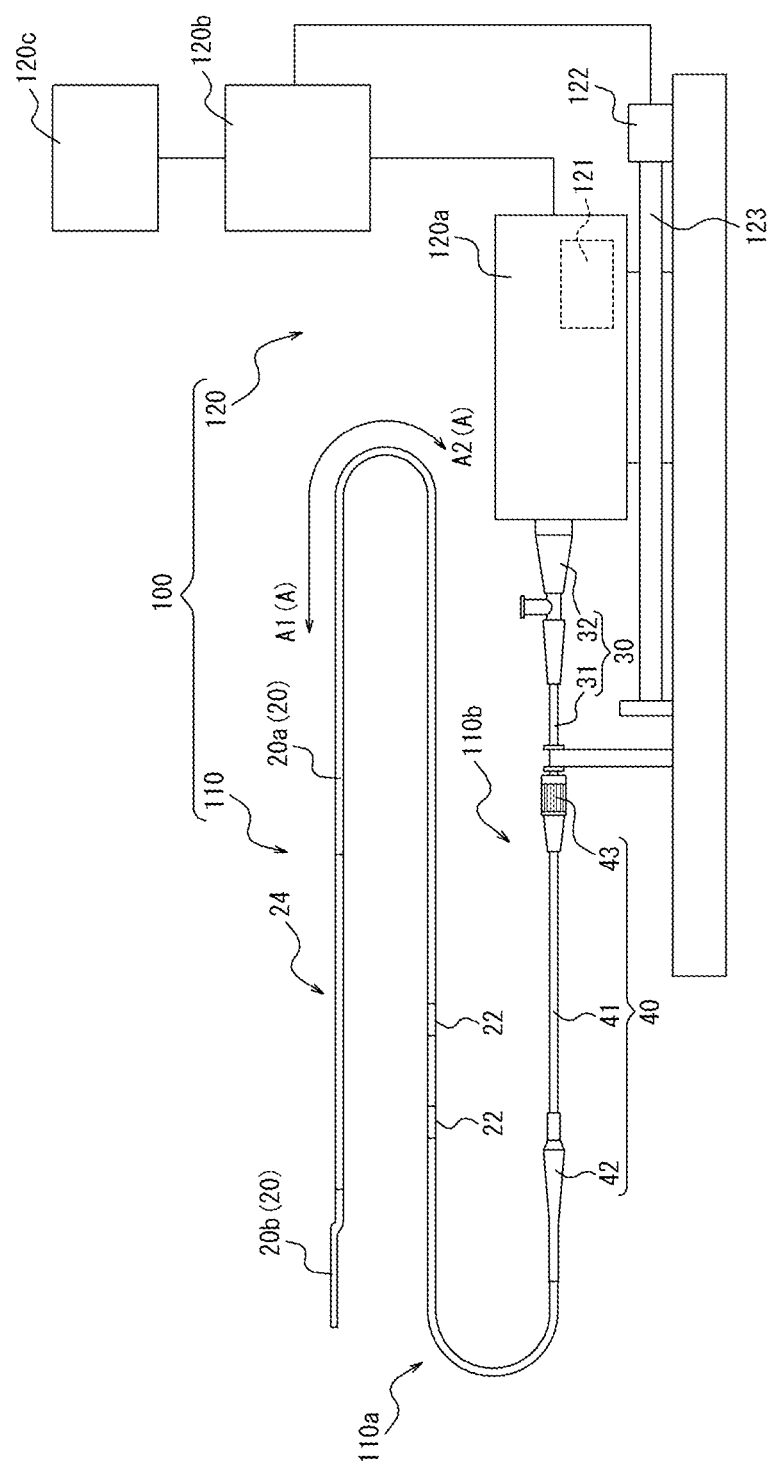
FIG. 1 is a view illustrating a state where a diagnostic imaging catheter including an ultrasound transducer serving as one embodiment of the disclosure is connected to an external device.

Set forth below with reference to the accompanying drawings is a detailed description of embodiments of an ultrasound transducer representing examples of the inventive ultrasound transducer disclosed here. Elements and portions or parts common in the respective drawings are denoted with the same reference numerals.

Firstly, one example of a diagnostic imaging apparatus to which an ultrasound transducer according to the disclosure can be applied will be described. FIG. 1 is a view illustrating a diagnostic imaging apparatus 100 that is provided with an ultrasound transducer 11 as one embodiment.

Figure 2:
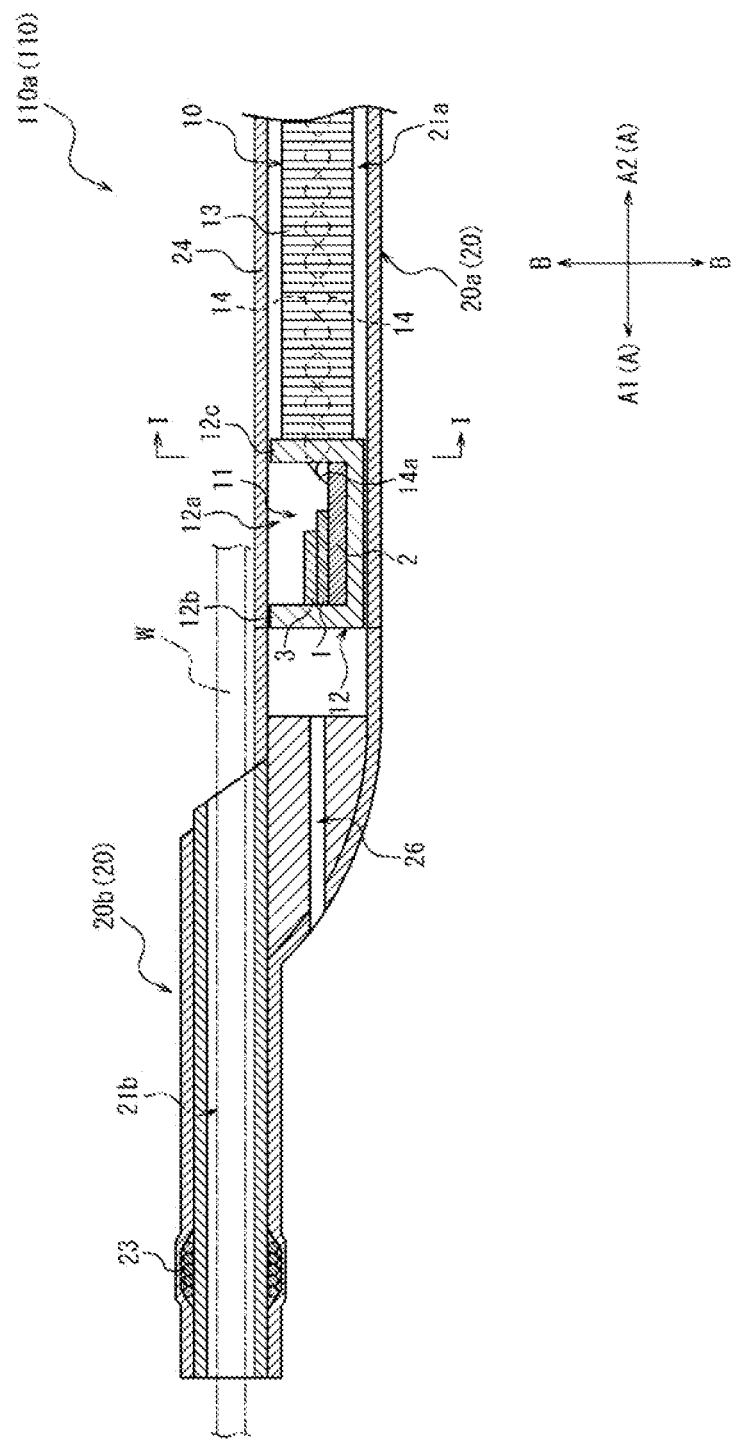
FIG. 2 is a cross-sectional view illustrating a cross section parallel to a longitudinal direction in a distal end portion of the diagnostic imaging catheter illustrated in FIG. 1.
Figure 3:
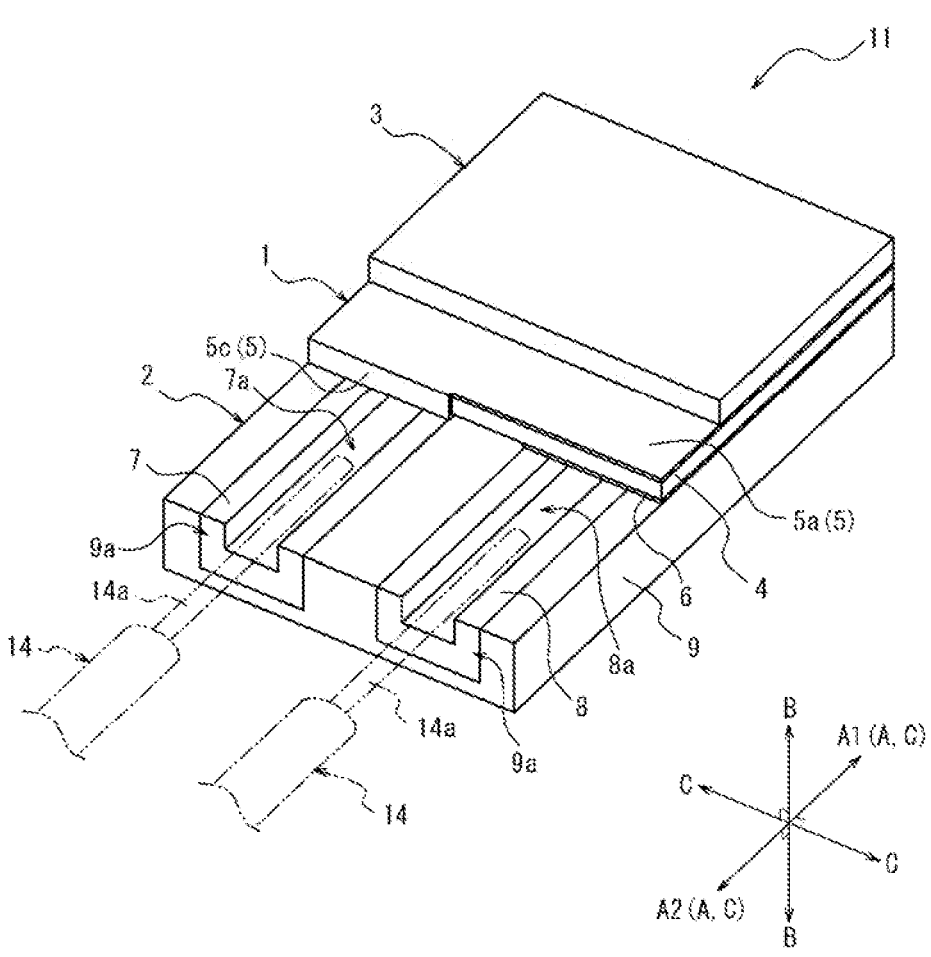
FIG. 3 is a view illustrating the ultrasound transducer of the diagnostic imaging catheter illustrated in FIG. 1.
Figure 4:
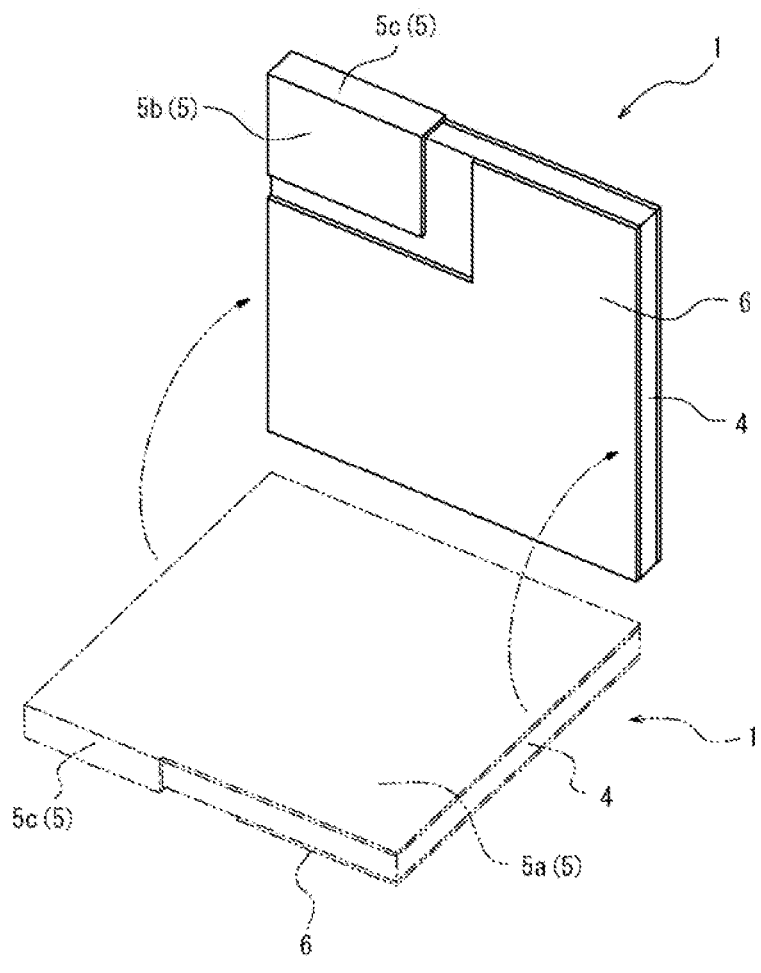
FIG. 4 is a view illustrating a rear surface of a piezoelectric element in the ultrasound transducer illustrated in FIG. 3.
Figure 5:
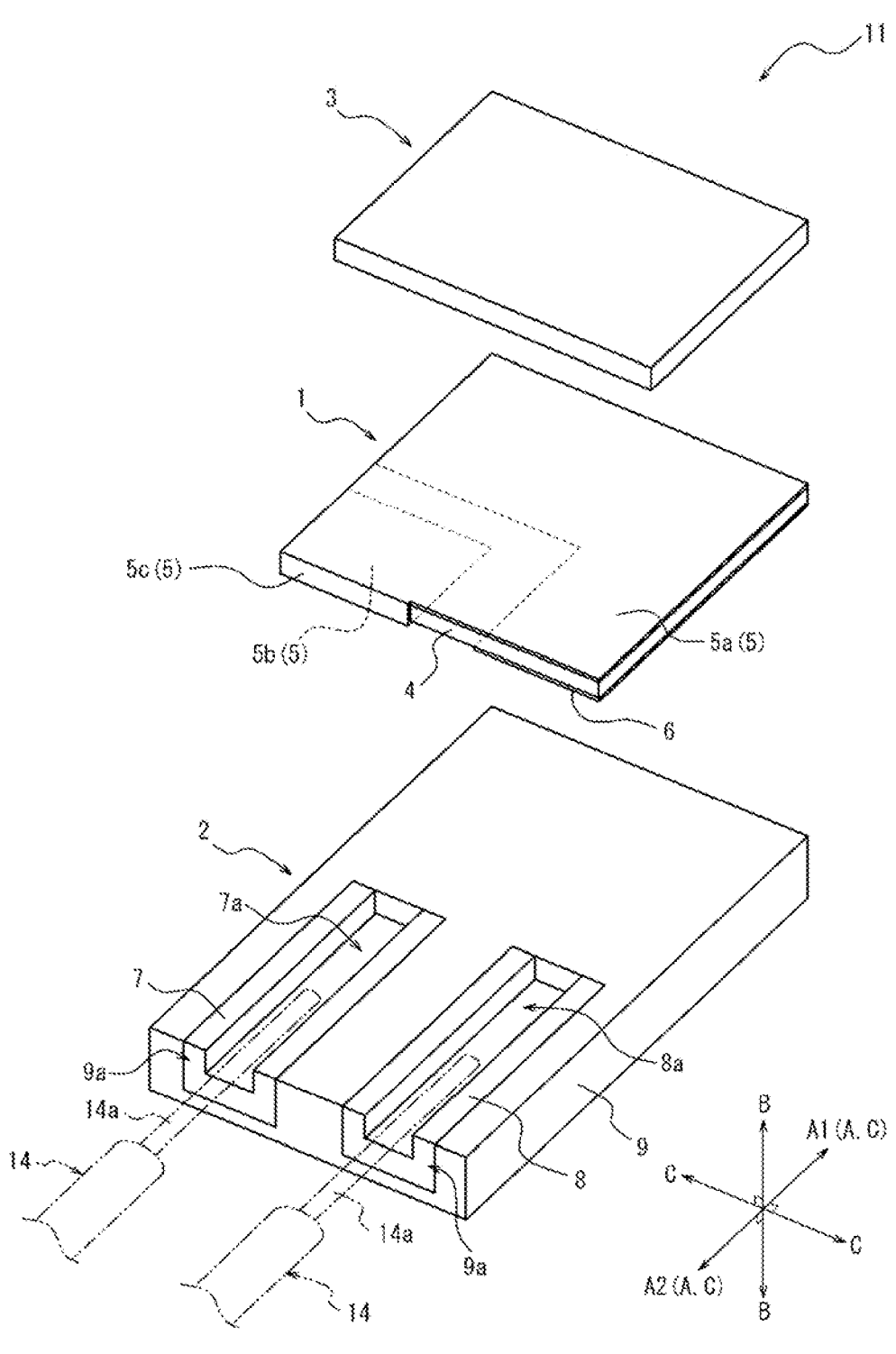
FIG. 5 is an exploded perspective view of the ultrasound transducer illustrated in FIG. 3.

The diagnostic imaging apparatus 100 is provided with a diagnostic imaging catheter 110 and an external device 120. FIG. 1 illustrates a state where the diagnostic imaging catheter 110 is connected to the external device 120. FIG. 2 is a cross-sectional view illustrating a cross section parallel to a longitudinal direction A in a distal end portion of the diagnostic imaging catheter 110. FIG. 3 is a view illustrating the ultrasound transducer 11. FIG. 3 illustrates positions of electric signal lines 14 that are connected to the ultrasound transducer 11 by chain double-dashed lines, for convenience of explanation. FIG. 4 is a view illustrating a rear surface of a piezoelectric element 1 in the ultrasound transducer 11 illustrated in FIG. 3. FIG. 5 is an exploded perspective view of the ultrasound transducer 11 illustrated in FIG. 3. FIG. 5 also illustrates the positions of the electric signal lines 14

Figure 6:
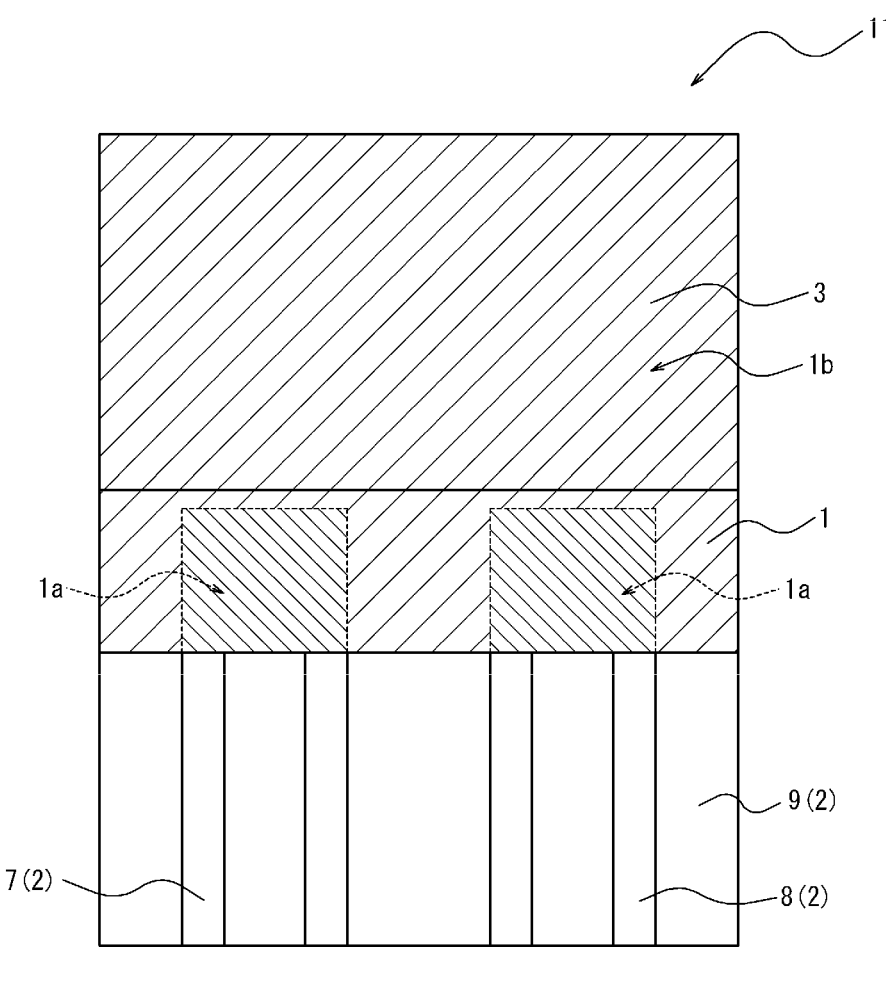
FIG. 6 is a view illustrating a region where the piezoelectric element and a support member overlap each other in a thickness direction, in the ultrasound transducer illustrated in FIG. 3.
Figure 6:
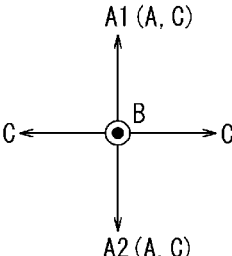

4 that are connected to the ultrasound transducer 11 by chain double-dashed lines, for convenience of explanation. Moreover, for convenience of explanation, FIG. 5 illustrates a position of a rear surface electrode layer 5b of a first electrode 5 and a position of a second electrode 6, of the piezoelectric element 1, by dashed lines. FIG. 6 is a view illustrating a region where the piezoelectric element 1 and a support member 2 overlap each other in a thickness direction B, in the ultrasound transducer 11 illustrated in FIG. 3.

Diagnostic Imaging Catheter 110

The diagnostic imaging catheter 110 is applied to Intravascular Ultrasound (abbreviated to "IVUS"). As illustrated in FIG. 1, the diagnostic imaging catheter 110 is connected to the external device 120, and the diagnostic imaging catheter 110 is driven by the external device. More specifically, the diagnostic imaging catheter 110 in the embodiment is connected to a drive unit 120a of the external device 120.

Hereinafter, for convenience of explanation, in the diagnostic imaging catheter 110, a side that is inserted into a living body in the longitudinal direction A of the diagnostic imaging catheter 110 is described as a "distal end side", and an opposite side of the diagnostic imaging catheter 110 is described as a "proximal end side". Moreover, a direction from the proximal end side toward the distal end side of the diagnostic imaging catheter 110 is described as an "insertion direction A1" in some cases. Moreover, a direction from the distal end side toward the proximal end side of the diagnostic imaging catheter 110 is described as an "extraction direction A2" in some cases.

As illustrated in FIG. 1, the diagnostic imaging catheter 110 is provided with an insertion portion 110a and an operation portion 110b. The insertion portion 110a is a part in the diagnostic imaging catheter 110 that is inserted into the living body and used in the living body. The operation portion 110b is a part in the diagnostic imaging catheter 110 that is operated outside the living body in the state where the insertion portion 110a is inserted into the living body. In the diagnostic imaging catheter 110 in the embodiment, a portion at a further distal end side than a distal end side connector 42 (see FIG. 1), is the insertion portion 110a, and a portion at a further proximal end side than the distal end side connector 42 is the operation portion 110b.

As illustrated in FIGS. 1 and 2, the insertion portion 110a is provided with an ultrasound probe 10 and a sheath 20.

As illustrated in FIG. 1, the operation portion 110b is provided with an inner tubular member 30 and an outer tubular member 40. The inner tubular member 30 holds an end portion at a proximal end side of the ultrasound probe 10. The outer tubular member 40 holds an end portion at a proximal end side of the sheath 20. In accordance with an exemplary embodiment, the inner tubular member 30 moves in a central axis direction inside the outer tubular member 40 to enable the ultrasound probe 10 to move in the longitudinal direction A inside the sheath 20. In addition, a drive shaft 13 and the electric signal lines 14, which are parts of the ultrasound probe 10, extend through inner portions of the inner tubular member 30 and the outer tubular member 40 over not only a region of the insertion portion 110a but also a region of the operation portion 110b, in the longitudinal direction A. In other words, a part of the operation portion 110b in the embodiment includes, in addition to the inner tubular member 30 and the outer tubular member 40, the ultrasound probe 10.

Ultrasound Probe 10

As illustrated in FIG. 2, the ultrasound probe 10 includes the ultrasound transducer 11, a housing 12, the drive shaft 13, and the electric signal lines 14.

As illustrated in FIG. 3, the ultrasound transducer 11 includes the piezoelectric element 1, the support member 2, and an acoustic matching member 3. Specifically, the piezoelectric element 1 includes a flat piezoelectric body (or planar surface piezoelectric body) 4, the first electrode 5 that is laminated on at least one side of the piezoelectric body 4 in the thickness direction B, and the second electrode 6 that is laminated on at least the other side of the piezoelectric body 4 in the thickness direction B. Hereinafter, for convenience of explanation, one side of the piezoelectric body 4 in the thickness direction B to which at least a part of the first electrode 5 is provided is described as a "surface side of the piezoelectric element 1". Moreover, for convenience of explanation, the other side of the piezoelectric body 4 in the thickness direction B to which at least a part of the second electrode 6 is provided is described as a "rear surface side of the piezoelectric element 1". The surface side of the piezoelectric element 1 is a side at which transmission and reception of ultrasound are performed. Moreover, the rear surface side of the piezoelectric element 1 is an opposite side to the side at which transmission and reception of ultrasound is performed.

The piezoelectric body 4 of the piezoelectric element 1 can include, for example, a piezoelectric ceramic sheet. Examples of the materials for the piezoelectric ceramic sheet can include piezoelectric ceramic materials such as lead titanate zirconate (PZT) and lithium niobate. The piezoelectric body 4 may be formed of crystal, rather than the piezoelectric ceramic material.

The first electrode 5 and the second electrode 6 of the piezoelectric element 1 can be formed by being laminated as electrode layers respectively on the both surfaces of the piezoelectric body 4 in the thickness direction B, for example, by an ion plating method using a mask material, a vapor deposition method, and a sputtering method. Examples of the materials for the first electrode 5 and the second electrode 6 can include metals such as silver, chromium, copper, nickel, and gold, and a laminated body of these metals (i.e., silver, chromium, copper, nickel, and/or gold).

As illustrated in FIGS. 3 and 4, the second electrode 6 in the embodiment is formed only on the rear surface side of the piezoelectric element 1.

In contrast, as illustrated in FIGS. 3 and 4, the first electrode 5 in the embodiment can include a folded electrode. Specifically, the folded electrode of the first electrode 5 in the embodiment is provided with a surface electrode layer 5a, the rear surface electrode layer 5b, and an interlock conductive portion 5c. The surface electrode layer 5a is positioned at the surface side of the piezoelectric element 1. The rear surface electrode layer 5b is positioned at the rear surface side of the piezoelectric element 1. The interlock conductive portion 5c interlocks the surface electrode layer 5a and the rear surface electrode layer 5b to each other. In other words, the first electrode 5 in the embodiment is formed from the surface side over the rear surface side of the piezoelectric element 1. The first electrode 5 is a folded electrode, so that the rear surface electrode layer 5b of the first electrode 5, and the second electrode 6 can be disposed together on the rear surface side of the piezoelectric element 1. Accordingly, compared with a case where the first electrode and the second electrode are respectively disposed only on the different surfaces of the piezoelectric element, connection work of the electric signal lines 14 to the first electrode 5 and the second electrode 6 can be performed only at one surface side of the piezoelectric element 1.

As illustrated in FIG. 6, the piezoelectric element 1 is provided with a first portion 1a including a portion overlapping a first terminal 7 and a portion overlapping a second terminal 8 of the support member 2, which is described later, in the thickness direction B, and a second portion 1b excluding the first portion 1a, in the thickness direction B.

Moreover, as illustrated in FIG. 6, in a plan view in which the ultrasound transducer 11 is seen in the thickness direction B, an outer shape (i.e., outer periphery) of the piezoelectric element 1 may preferably be square as in the embodiment, rather than being rectangular. In this manner, the straightness of ultrasound can be enhanced. Accordingly, as illustrated in FIG. 6, vertical (up-and-down direction in FIG. 6) and transverse (right-and-left direction in FIG. 6) lengths of the piezoelectric element 1 are preferably approximately the same. In addition, in a case of the compact ultrasound transducer 11 that is used inside a blood vessel, it is preferable to increase the output of ultrasound. Therefore, it is preferable to largely secure the second portion 1b, which is a portion of the piezoelectric element 1 that mainly vibrates. As in the foregoing, the piezoelectric element 1 preferably has a square outer shape in a plan view illustrated in FIG. 6, and an area in the second portion 1b of the piezoelectric element 1 is preferably larger than an area in the first portion 1a of the piezoelectric element 1.

As illustrated in FIG. 3, the support member 2 supports the piezoelectric element 1. Moreover, as illustrated in FIGS. 3 and 5, the support member 2 is provided with the first terminal 7 that is connected to the first electrode 5 of the piezoelectric element 1, and the second terminal 8 that is connected to the second electrode 6 of the piezoelectric element 1. As illustrated in FIG. 3, the first terminal 7 and the second terminal 8 are respectively provided with portions that do not overlap the piezoelectric element 1 in the thickness direction B. The first terminal 7 and the second terminal 8 are provided to enable an electric contact between the first electrode 5 and the second electrode 6 of the piezoelectric element 1 to be drawn out to an outer side of the piezoelectric element 1. Therefore, for example, in a case where the electric signal lines 14 are difficult to be directly connected to the first electrode 5 and the second electrode 6 of the piezoelectric element 1, such as the downsized piezoelectric element 1, the use of the first terminal 7 and the second terminal 8 mentioned above makes it rather easy to electrically connect the electric signal lines 14 to the piezoelectric element 1.

As illustrated in FIG. 3, the support member 2 in the embodiment supports the piezoelectric element 1 from the rear surface side of the piezoelectric element 1. In other words, the support member 2 is laminated on the rear surface side of the piezoelectric element 1 so as to cover the rear surface side of the piezoelectric element 1.

Examples of the materials for the first terminal 7 and the second terminal 8 can include metals such as silver, chromium, copper, nickel, and gold, and a laminated body of these metals (i.e., chromium, copper, nickel and/or gold).

In accordance with an exemplary embodiment, the support member 2 in the embodiment is provided with a support main body portion 9 that is laminated on the rear surface side of the piezoelectric element 1. The support main body portion 9 covers at least the whole region on the rear surface side (i.e., an entirety of the rear surface side) of the piezoelectric body 4 of the piezoelectric element 1. The support main body portion 9 in the embodiment covers the whole region on the rear surface side (i.e., an entirety of the rear surface side) of the piezoelectric element 1. More specifically, the support main body portion 9 in the embodiment extends externally further than the piezoelectric element 1 in a direction C (hereinafter, described as "in-plane direction C".) orthogonal to the thickness direction B of the piezoelectric element 1. The first terminal 7 and the second terminal 8 in the embodiment are supported by the support main body portion 9.

The support main body portion 9 of the support member 2 can be a sound-absorbing body including rubber and epoxy resin in which metal powder such as tungsten powder is dispersed, for example. The support main body portion 9 of the support member 2 can absorb ultrasound as noise from the piezoelectric element 1. In other words, the support member 2 in the embodiment configures a sound absorbing layer that absorbs ultrasound of the piezoelectric element 1.

The sound absorbing layer as the support member 2 can be formed by a method in which the first terminal 7 and the second terminal 8 are disposed in advance on a sheet material forming the support main body portion 9, and the sheet material can be bonded to the piezoelectric element 1, or by other methods. The first terminal 7 and the second terminal 8 may be formed by being laminated on the sheet material forming the support main body portion 9, for example, by an ion plating method using a mask material, a vapor deposition method, and a sputtering method, and production methods thereof are not specially limited. Terminal members forming the first terminal 7 and the second terminal 8 may be joined to the support main body portion 9 by bonding or the like.

As illustrated in FIGS. 3 to 5, the first terminal 7 in the embodiment is connected to the rear surface electrode layer 5b of the first electrode 5 between the piezoelectric element 1 and the support main body portion 9. In other words, the piezoelectric element 1 and the support member 2 in the embodiment are laminated such that the rear surface electrode layer 5b of the first electrode 5 and the first terminal 7 are opposed to each other. Moreover, the first terminal 7 in the embodiment extends externally further than the piezoelectric element 1 in the in-plane direction C from a position between the piezoelectric element 1 and the support main body portion 9. In other words, the first terminal 7 is drawn out on a surface at the side of the piezoelectric element 1 in the thickness direction B of the support main body portion 9 (hereinafter, described as a "top surface of the support main body portion 9"), to a position that does not overlap the piezoelectric element 1 in the thickness direction B.

As illustrated in FIGS. 3 to 5, the second terminal 8 in the embodiment is connected to the second electrode 6 between the piezoelectric element 1 and the support main body portion 9. In other words, the piezoelectric element 1 and the support member 2 in the embodiment is laminated such that the second electrode 6 and the second terminal 8 are opposed to each other. Moreover, the second terminal 8 in the embodiment extends externally further than the piezoelectric element 1 in the in-plane direction C from the position between the piezoelectric element 1 and the support main body portion 9. In other words, the second terminal 8 is drawn out on the top surface of the support main body portion 9, to a position that does not overlap the piezoelectric element 1 in the thickness direction B.

In this manner, the first electrode 5 and the second electrode 6 of the piezoelectric element 1 can be respectively connected to the first terminal 7 and the second terminal 8 of the support member 2, at the rear surface side of the piezoelectric element 1. Therefore, connection locations for the electric signal lines 14 do not need to be secured at the surface side of the piezoelectric element 1 on which transmission and reception of ultrasound are performed, so that it is possible to suppress breakage of a portion in the ultrasound transducer 11 at the surface side of the piezoelectric element 1 on which transmission and reception of ultrasound are performed, in the connection of the electric signal lines 14. Moreover, the first terminal 7 and the second terminal 8 can be externally extended further than the piezoelectric element 1 in the in-plane direction C from the position between the piezoelectric element 1 and the support main body portion 9, so that the first terminal 7 and the second terminal 8 are in a state capable of being visually identified from the surface side of the piezoelectric element 1. Therefore, it is possible to execute the work of connecting the electric signal lines 14 to the first terminal 7 and the second terminal 8 while monitoring the connection locations by visual observation or the like, which can help suppress generation of a defective piece due to a connection failure.

Moreover, the first terminal 7 and the second terminal 8 in the embodiment are drawn out from a position overlapping the piezoelectric element 1 in the thickness direction B toward a proximal end side of the longitudinal direction A, in the diagnostic imaging catheter 110. Therefore, in the first terminal 7 and the second terminal 8 in the embodiment, a portion that does not overlap the piezoelectric element 1 in the thickness direction B is provided at the proximal end side relative to the piezoelectric element 1. Accordingly, as illustrated in FIG. 2, the first terminal 7 and the second terminal 8 in the embodiment can be rather easily connected to distal end portions 14a of the electric signal lines 14 that extends from a distal end of the drive shaft 13 into the housing 12.

In addition, as illustrated in FIG. 3, the first terminal 7 and the second terminal 8 in the embodiment extend to a circumferential edge in the in-plane direction C of the support member 2. More specifically, the first terminal 7 and the second terminal 8 in the embodiment extend to positions flush (i.e., completely level or even) with an end surface in the in-plane direction C of the support main body portion 9. In this manner, it is possible to rather easily connect the electric signal lines 14 to the first terminal 7 and the second terminal 8 from an outside of the ultrasound transducer 11.

Moreover, in the support member 2 in the embodiment, two grooves 9a are sectioned on the top surface of the support main body portion 9 opposed to the rear surface of the piezoelectric element 1. A transverse cross section of the groove 9a in the embodiment is a rectangular shape, and may be another transverse cross-sectional shape such as a V-character shape or a circular shape, for example. The first terminal 7 and the second terminal 8 in the embodiment are disposed inside the grooves 9a of the support main body portion 9. Moreover, a top surface of the first terminal 7 and a top surface of the second terminal 8 opposing to the rear surface of the piezoelectric element 1 are disposed so as to be flush (i.e., completely level or even) with the top surface of the support main body portion 9. Accordingly, the piezoelectric element 1 and the support member 2 are laminated on each other, so that the first electrode 5 and the second electrode 6 of the piezoelectric element 1 can be respectively come into contact with the first terminal 7 and the second terminal 8 of the support member 2, and the position stability on the support member 2 of the piezoelectric element 1 can be improved. The first electrode 5 and the second electrode 6 of the piezoelectric element 1 are respectively connected to the first terminal 7 and the second terminal 8 of the support member 2, using a conductive adhesive or the like.

In accordance with an exemplary embodiment, the top surface of the first terminal 7 and the top surface of the second terminal 8 opposing to the rear surface of the piezoelectric element 1 may be respectively disposed inside the grooves 9a without protruding from the top surface of the support main body portion 9. In such a case, portions between the first electrode 5 and the second electrode 6 of the piezoelectric element 1 and the first terminal 7 and the second terminal 8 of the support member 2, may be filled with a conductive material such as the abovementioned conductive adhesive. In this manner, an effect similar to the abovementioned effect by making the top surface of the first terminal 7, the top surface of the second terminal 8, and the top surface of the support main body portion 9 flush (i.e., completely level or even) with one another can be obtained.

In addition, as illustrated in FIGS. 3 and 5, a groove 7a that houses the electric signal line 14 is sectioned in the first terminal 7 in the embodiment. In accordance with an embodiment, the groove 7a is sectioned in the first terminal 7, so that it is possible to connect the electric signal line 14 to the first terminal 7 in a state where the electric signal line 14 is positioned inside the groove 7a. Therefore, the efficiency of the connection work between the electric signal line 14 and the first terminal 7 can be improved.

As illustrated in FIGS. 3 and 5, a groove 8a that houses the electric signal line 14 is also sectioned in the second terminal 8 in the embodiment. Such the groove 8a is sectioned in the second terminal 8, so that it is possible to connect the electric signal line 14 to the second terminal 8 in a state where the electric signal line 14 is positioned inside the groove 8a. Therefore, the efficiency of the connection work between the electric signal line 14 and the second terminal 8 can be improved.

In this manner, the grooves (the grooves 7a and 8a in the embodiment) are respectively provided in the first terminal 7 and the second terminal 8 to make it rather easy to connect the electric signal lines 14 to the respective terminals (the first terminal 7 and the second terminal 8 in the embodiment). Although each of transverse cross-sectional shapes of the groove 7a and the groove 8a in the embodiment is a rectangular shape, each groove may have another transverse cross-sectional shape such as a V-character shape or a circular shape, for example. Moreover, the groove 7a and the groove 8a may also preferably extend to positions that are flush (i.e., completely level or even) with the end surface in the in-plane direction C of the support main body portion 9. In this manner, the electric signal lines 14 are rather easily to be positioned.

Figure 7:
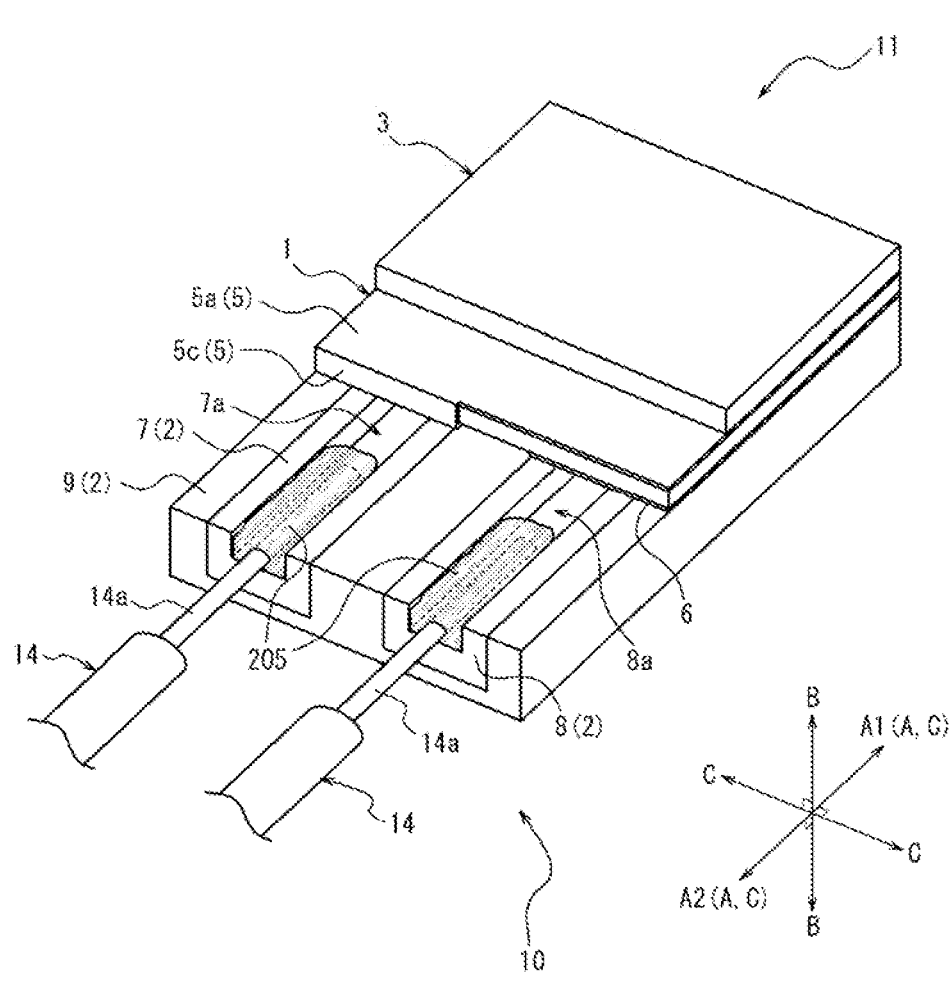
FIG. 7 is a view illustrating an overview of a process of connecting the electric signal line to a first terminal.

An example of a method of connecting the electric signal line 14 to the first terminal 7 will be described. FIG. 7 is a view illustrating an overview of a process of connecting the electric signal line 14 to the first terminal 7. Firstly, a connection portion 14a including a conductive wire from which a coating material is removed is formed on an end portion of the electric signal line 14. Moreover, the groove 7a of the first terminal 7 is filled with a solder paste 205. The groove 7a may be filled with a preliminary solder in place of the solder paste 205. In this state, the connection portion 14a of the electric signal line 14 is disposed on the solder paste 205 that is filled in the groove 7a of the first terminal 7. The connection portion 14a of the electric signal line 14 may be buried in the solder paste 205 that is filled in the groove 7a. A preliminary solder or a solder paste may be further applied so as to sandwich the connection portion 14a with the solder paste 205. Next, the solder paste 205 and the preliminary solder are heated with hot air to be melted, and the connection portion 14a is connected to the first terminal 7 inside the groove 7a. In this manner, the electric signal line 14 can be connected to the first terminal 7.

Although the connection method between the electric signal line 14 and the first terminal 7 is indicated herein, the same applies to a connection method between the electric signal line 14 and the second terminal 8.

As described above, the piezoelectric element 1 is provided with the first portion 1a including the portion overlapping the first terminal 7 and the portion overlapping the second terminal 8 in the thickness direction B, and the second portion 1b excluding the first portion 1a (see FIG. 6). As illustrated in FIG. 6, in the embodiment, the whole region on the rear surface side (i.e., an entirety of the rear surface side) of the second portion 1b of the piezoelectric element 1 can be covered with the support main body portion 9. With such a configuration, the support main body portion 9 is disposed to the whole rear surface (i.e., an entirety of the rear surface) of the second portion 1b that is a portion in which the piezoelectric element 1 mainly vibrates. Therefore, ultrasound as noise from the piezoelectric element 1 can be more reliably absorbed by the support main body portion 9.

As illustrated in FIG. 3, the acoustic matching member 3 is laminated so as to cover a part of the surface side of the piezoelectric element 1. More specifically, the acoustic matching member 3 in the embodiment is laminated so as to cover a greater part (for example, 80% or more) of the surface side of the second portion 1b of the piezoelectric element 1, but is not limited to this configuration, and may be laminated so as to cover the whole region of the surface side (i.e., an entirety of the surface side) of the second portion 1b of the piezoelectric element 1. Moreover, the acoustic matching member 3 may be laminated so as to cover the surface sides of both of the first portion 1a and the second portion 1b of the piezoelectric element 1, or may be laminated so as to cover the whole region of the surface side (i.e., an entirety of the surface side) of the piezoelectric element 1.

The acoustic matching member 3 is provided to make it possible to enhance the propagation efficiency of ultrasound to a subject. In other words, the acoustic matching member 3 in the embodiment configures an acoustic matching layer that enhance the propagation efficiency of ultrasound.

The acoustic matching layer as the acoustic matching member 3 can be formed by a method of bonding a sheet material forming the acoustic matching layer to the piezoelectric element 1, a method in which a liquid acoustic integrity material forming the acoustic matching layer is applied and cured, or the like. Examples of the materials for the acoustic matching member 3 can include a resin material such as epoxy resin. Moreover, the acoustic matching member 3 may include a laminated body of a resin layer including a resin material.

As illustrated in FIG. 2, the housing 12 houses the ultrasound transducer 11 inside of the housing 12. A proximal end side of the housing 12 is connected to the drive shaft 13. The housing 12 can have a shape in which an opening portion 12a is provided to a part of a circumferential wall of a cylindrical metal pipe with both end portions in an axis direction being closed, and can be formed, for example, by shaving off a metal lump, metallic powder injection molding (MIM), or the like.

In accordance with an exemplary embodiment, the housing 12 in the embodiment is provided with a distal end wall portion 12b that is positioned at a further distal end side than the above-mentioned opening portion 12a, and a proximal end wall portion 12c that is positioned at a further proximal end side than the above-mentioned opening portion 12a. Both end portions in the axis direction (i.e., axial direction) of an internal space of the housing 12 in the embodiment are respectively closed by the distal end wall portion 12*b* and the proximal end wall portion 12*c*. The housing 12 is closed at the distal end side and the proximal end side of the ultrasound transducer 11 to make it possible to suppress the false detection of ultrasound, and to improve the accuracy of an image diagnosis. As illustrated in FIG. 2, the electric signal lines 14 that extend inside the drive shaft 13 penetrate through the proximal end wall portion 12*c* and extend into the housing 12.

The drive shaft 13 includes a tubular body having flexibility. In an inside of the drive shaft 13, the electric signal lines 14 to be connected to the ultrasound transducer 11 are disposed. The drive shaft 13 can include, for example, a multilayer coil in which winding directions around the axis are different from each other. Examples of the materials for the multilayer coil can include stainless steel and a nickel-titanium (Ni—Ti) alloy. Even when the two electric signal lines 14 include a double spiral twisted pair cable, such the drive shaft 13 is employed to make it possible to enhance the shield property and reduce an influence by noise generated from the electric signal lines 14.

The drive shaft 13 extends through insides of the inner tubular member 30 and the outer tubular member 40 to a hub 32, which is described later, that is positioned at a proximal end portion of the inner tubular member 30. In other words, in the longitudinal direction A, the drive shaft 13 extends from a distal end portion of the insertion portion 110*a* to a proximal end portion of the operation portion 110*b*.

As illustrated in FIG. 2, the electric signal line 14 extends inside the drive shaft 13, and is electrically connected to the ultrasound transducer 11 and the external device 120. In other words, similar to the drive shaft 13, in the longitudinal direction A, the electric signal line 14 extends from the distal end portion of the insertion portion 110*a* to the proximal end portion of the operation portion 110*b*. The plurality (two in the embodiment) of the electric signal lines 14 are provided, each of the electric signal lines 14 is connected via the first terminal 7 or the second terminal 8 of the above-mentioned support member 2 to the first electrode 5 or the second electrode 6 of the above-mentioned piezoelectric element 1. The plurality of the electric signal lines 14 can include, for example, a twisted pair cable in which the two electric signal lines 14 are twisted to each other. Each of the electric signal lines 14 can be a flexible fine line member having an outer diameter larger than 0 mm and equal to or smaller than 0.1 mm and having flexibility. Each of the electric signal lines 14 can include, for example, a conductive wire having an outer diameter larger than 0 mm and equal to or smaller than 0.05 mm, and a coating material that is formed of an insulating material and covers the surrounding of the conductive wire. In such the electric signal line 14, the connection portion 14*a* (see FIG. 3, FIG. 5) including an exposed conductive wire from which the coating material is removed is connected to the piezoelectric element 1.

In the embodiment, the connection portions 14*a* of the two electric signal lines 14 are respectively connected to the first terminal 7 and the second terminal 8 of the support member 2 using soldering, a conductive adhesive, or the like (see FIG. 7). Accordingly, the two electric signal lines 14 are respectively electrically connected to the first electrode 5 and the second electrode 6 of the piezoelectric element 1 via the first terminal 7 and the second terminal 8 of the support member 2. More specifically, the two electric signal lines 14 are respectively connected to the first terminal 7 and the second terminal 8 of the support member 2 at the further distal end side than the proximal end wall portion 12*c* of the housing 12.

Sheath 20

As illustrated in FIG. 2, in the sheath 20, a first hollow portion 21*a* and a second hollow portion 21*b* are sectioned. The ultrasound probe 10 is housed in the first hollow portion 21*a*. The ultrasound probe 10 can move forwardly and rearwardly in the longitudinal direction A inside the first hollow portion 21*a*. The second hollow portion 21*b* allows a guide wire W to be inserted through the second hollow portion 21*b*. In the embodiment, a tubular guide wire insertion portion 20*b* that sections the second hollow portion 21*b* is positioned in a state of being parallel to a distal end portion of a tubular main body portion 20*a* that sections the first hollow portion 21*a*. The main body portion 20*a* and the guide wire insertion portion 20*b* can be formed, for example, by joining tubular members different from each other by heat-welding or the like, but the embodiment is not limited to such the formation method.

In the main body portion 20*a*, markers 22 that are formed of an X-ray impermeable material having an X-ray contrast property are provided. In accordance with an exemplary embodiment, the guide wire insertion portion 20*b* as well, a marker 23 having an X-ray contrast property can be provided. The markers 22 and 23 can include, for example, a metal coil having a high X-ray impermeability, such as platinum, gold, iridium, and tungsten.

In a range in which the ultrasound transducer 11 moves in the longitudinal direction A of the sheath 20, a window portion 24 in which the permeability of ultrasound can be set higher than that in other sites is formed. More specifically, the window portion 24 in the embodiment is formed in the main body portion 20*a* in the sheath 20.

The window portion 24 and the guide wire insertion portion 20*b* of the main body portion 20*a* are formed of a material having flexibility, and the material of the window portion 24 and the guide wire insertion portion 20*b* of the main body portion 20*a* is not specially limited. Examples of the materials of the window portion 24 and the guide wire insertion portion 20*b* of the main body portion 20*a* can include various kinds of thermoplastic elastomers such as polyethylene, styrene, polyolefin, polyurethane, polyester, polyamide, polyimide, polybutadiene, trans polyisoprene, fluorine rubber, and chlorinated polyethylene, and a polymer alloy, a polymer blend, a laminated body, and the like in which one type or two or more types among these materials are combined can also be used.

At the further proximal end side than the window portion 24 of the main body portion 20*a*, a reinforcing portion that is reinforced by a material having rigidity higher than that of the window portion 24 is included. The reinforcing portion is formed, for example, in such a manner that a reinforcing material in which a metal wire made of stainless steel or the like is braided in a mesh shape is disposed to a tubular member such as resin having flexibility. The abovementioned tubular member can be formed of a material similar to that of the window portion 24.

In accordance with an exemplary embodiment, a hydrophilic lubricant coating layer indicating lubricity when being wet is preferably disposed to an outer surface of the sheath 20.

In a distal end portion of the main body portion 20*a* of the sheath 20, a communication hole 26 that communicates an inside and an outside of the first hollow portion 21*a* with each other is formed. In priming, gas inside the main body portion 20*a* can be ejected through the communication hole 26.

Inner Tubular Member 30 and Outer Tubular Member 40

As illustrated in FIG. 1, the inner tubular member 30 is provided with an inner tube 31 and the hub 32.

The inner tube 31 is inserted into the outer tubular member 40 so as to be capable of moving forwardly and rearwardly.

The hub 32 is provided on a proximal end side of the inner tube 31.

As illustrated in FIG. 1, the outer tubular member 40 is provided with an outer tube 41, the distal end side connector 42, and a proximal end side connector 43. The outer tube 41 is positioned at a radially outer side of the inner tube 31, and the inner tube 31 moves forwardly and rearwardly inside the outer tube 41. The distal end side connector 42 connects a proximal end portion of the main body portion 20a of the sheath 20 to a distal end portion of the outer tube 41. The proximal end side connector 43 is provided to a proximal end portion of the outer tube 41, and is configured to receive the inner tube 31 in the outer tube 41.

The drive shaft 13 and the electric signal lines 14 of the above-mentioned ultrasound probe 10 extend to the main body portion 20a of the sheath 20, the outer tubular member 40 that is connected to the proximal end side of the main body portion 20a, and the hub 32 that is positioned at a proximal end portion of the inner tubular member 30 a part of which is inserted into the outer tubular member 40.

The ultrasound probe 10 and the inner tubular member 30 mentioned above are connected to each other so as to respectively and integrally move forwardly and rearwardly in the longitudinal direction A. Therefore, for example, when an operation of pushing the inner tubular member 30 toward the insertion direction A1 is performed, the inner tubular member 30 is pushed down into the outer tubular member 40 toward the insertion direction A1. When the inner tubular member 30 is pushed down into the outer tubular member 40 toward the insertion direction A1, the ultrasound probe 10 connected to the inner tubular member 30 moves in the insertion direction A1 inside the main body portion 20a of the sheath 20. Conversely, an operation of drawing out the inner tubular member 30 toward the extraction direction A2 is performed, the inner tubular member 30 is drawn out from the inside of the outer tubular member 40 toward the extraction direction A2. When the inner tubular member 30 is drawn out from the inside of the outer tubular member 40 toward the extraction direction A2, the ultrasound probe 10 connected to the inner tubular member 30 moves in the extraction direction A2 inside the main body portion 20a of the sheath 20.

When the inner tubular member 30 is most pushed down in the insertion direction A1, a distal end portion of the inner tubular member 30 reaches the vicinity of the distal end side connector 42 of the outer tubular member 40. At this time, the ultrasound transducer 11 of the ultrasound probe 10 is positioned in the vicinity of a distal end of the main body portion 20a of the sheath 20.

At the distal end portion of the inner tubular member 30, a stopper portion that helps prevent the inner tubular member 30 from protruding to a further distal end side than the outer tubular member 40 and help prevent the outer tubular member 40 from slip off to the proximal end side when the inner tubular member 30 is pulled to the most proximal end side, is provided. The stopper portion is not specially limited as long as the stopper portion has a configuration that can implement the abovementioned functions, and may include a wall portion that collides against the outer tubular member 40 in the longitudinal direction A, at a prescribed position, for example.

At a proximal end of the hub 32 of the inner tubular member 30, a connector portion that is mechanically and electrically connected to the external device 120 is provided. In other words, the diagnostic imaging catheter 110 is mechanically and electrically connected to the external device 120 by the connector portion that is provided to the hub 32 of the inner tubular member 30. More specifically, the electric signal lines 14 of the ultrasound probe 10 extend from the ultrasound transducer 11 to the connector portion of the hub 32, and the connector portion of the hub 32 in a state of being connected to the external device 120 electrically connects the ultrasound transducer 11 and the external device 120 to each other. A reception signal in the ultrasound transducer 11 is transmitted to the external device 120 via the connector portion of the hub 32, and is displayed as an image after being subjected to prescribed processing.

External Device 120

As illustrated in FIG. 1, the external device 120 can include a motor 121 that is a driving power source for rotating the drive shaft 13, and a motor 122 that is a driving power source for moving the drive shaft 13 in the longitudinal direction A. The rotation movement of the motor 122 can be converted into axial movement by a ball screw 123 connected to the motor 122.

In accordance with an exemplary embodiment, the external device 120 in the embodiment is provided with the drive unit 120a, a controller 120b that is electrically connected to the drive unit 120a in a wired or wireless manner, and a monitor 120c that can display an image generated by the controller 120b on the basis of the reception signal received from the diagnostic imaging catheter 110. The motor 121, the motor 122, and the ball screw 123 in the embodiment mentioned above are provided to the drive unit 120a. A motion of the drive unit 120a is controlled by the controller 120b. The controller 120b can be configured by a processor including a CPU and a memory.

The configuration of the external device 120 is not limited to that indicated in the embodiment, and may be, for example, a configuration of further including an external input unit such as a key board.

The configuration of the ultrasound transducer according to the disclosure is not limited to the specific configuration specified in the above-mentioned embodiment, but various modifications and changes are possible without deviating from the scope of the claims. In the ultrasound transducer 11 in the embodiment, the first electrode 5 includes a folded electrode, however, a configuration in which neither the first electrode 5 nor the second electrode 6 is a folded electrode but each of the first electrode 5 and the second electrode 6 is laminated only on one surface may be employed. In addition, in place of the first electrode 5, the second electrode 6 may include a folded electrode. In accordance with an exemplary embodiment, when the first electrode 5 is configured as a folded electrode as in the embodiment, the first electrode 5 and the second electrode 6 of the piezoelectric element 1 are respectively connected to the first terminal 7 and the second terminal 8 of the support member 2, at the rear surface side of the piezoelectric element 1. Therefore, as described above, connection locations for the electric signal lines 14 do not need to be secured at the surface side of the piezoelectric element 1 on which transmission and reception of ultrasound are performed, so that it is possible to suppress breakage of a portion in the ultrasound transducer 11 at the surface side of the piezoelectric element 1 on which transmission and reception of ultrasound are performed, in the connection of the electric signal lines 14.

Figure 8:
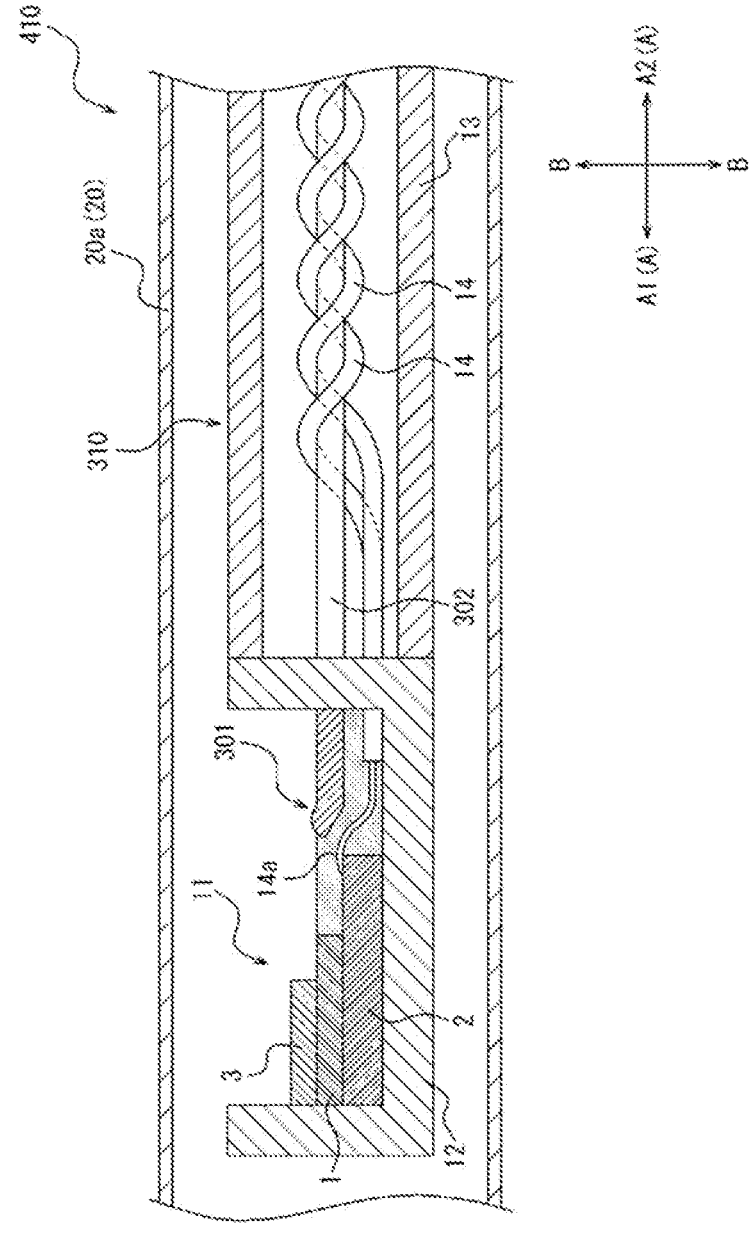
FIG. 8 is a cross-sectional view illustrating a part of a diagnostic imaging catheter including an ultrasound transducer as one embodiment of the disclosure.

In addition, as for the ultrasound probe to which the ultrasound transducer according to the disclosure can be applied, the configuration is not limited to the configuration of the ultrasound probe 10 indicated in the above-mentioned embodiment. The ultrasound probe 10 in the above-mentioned embodiment has a configuration in which only the ultrasound transducer 11 is provided as an imaging core that allows an intravascular ultrasound diagnosis, however, the configuration is not limited to this configuration but a configuration in which an optical transmitter and receiver that allows optical coherence tomography (abbreviated to "OCT") is further included may be employed, for example. FIG. 8 is a cross-sectional view illustrating a part of a diagnostic imaging catheter 410 that is provided with an ultrasound probe 310 including the ultrasound transducer 11 and an optical transmitter and receiver 301. The ultrasound probe 310 illustrated in FIG. 8 is different from the above-mentioned ultrasound probe 10 in that a configuration that allows the optical coherence tomography is added.

Specifically, in the ultrasound probe 310 illustrated in FIG. 8, in addition to the ultrasound transducer 11, the optical transmitter and receiver 301 is disposed inside the housing 12. The optical transmitter and receiver 301 continuously transmits light (measurement light) to be transferred from an optical fiber cable as a light signal line 302 extending in the drive shaft 13, into a biological lumen, and continuously receives reflected light from a biological tissue in the biological lumen. The optical transmitter and receiver 301 transmits the received reflected light to the external device 120 through the light signal line 302 (see FIG. 1). The controller 120b (see FIG. 1) of the external device 120 causes the reflected light obtained by the measurement and the reference light obtained by separating the light from the light source to interfere with each other to generate interference light data. Moreover, the controller 120b of the external device 120 generates a light tomographic image on the basis of the generated interference light data, and causes the monitor 120c (see FIG. 1) to display the light tomographic image.

As illustrated in FIG. 8, inside the drive shaft 13, the plurality of the electric signal lines 14 are wound around the light signal line 302 in a spiral shape, and the plurality of the electric signal lines 14 extend parallel to one another. More specifically, the two electric signal lines 14 illustrated in FIG. 8 extend double helically in the surrounding of the optical fiber cable as the light signal line 302 that extends in the longitudinal direction A.

The detailed description above describes versions of an ultrasound transducer representing examples of the inventive ultrasound transducer device disclosed here. The invention is not limited, however, to the precise embodiment and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. An ultrasound transducer comprising:
a piezoelectric element, the piezoelectric element includes a flat piezoelectric body, a first electrode that is laminated on at least one side of the piezoelectric body in a thickness direction, and a second electrode that is laminated on at least the other side of the piezoelectric body in the thickness direction;

a support member, the support member includes a first terminal that is connected to the first electrode of the piezoelectric element, and a second terminal that is connected to the second electrode of the piezoelectric element; and
the first terminal and the second terminal respectively include portions that do not overlap the piezoelectric element in the thickness direction,
wherein the support member includes a support main body portion that is laminated on the piezoelectric element at the other side in the thickness direction, and extends externally further than the piezoelectric element in a direction orthogonal to the thickness direction;
the first terminal and the second terminal are supported by the support main body portion, and wherein the support member is configured as a sound absorbing member;
electrical signal lines connected to the first electrode and the second electrode; and
wherein the support member includes a support main body, the support main body having a pair of grooves that receive the electrical signal lines connected to the first electrode and the second electrode, the pair of grooves being sectioned on a top surface of the support main body portion opposed to a surface of the piezoelectric element;
and an acoustic matching member, the acoustic matching member arranged on one side of the piezoelectric element, and the support member arranged on an opposite side of the piezoelectric element.

2. The ultrasound transducer according to claim 1, wherein the first electrode of the piezoelectric element includes a surface electrode layer that is positioned at the one side in the thickness direction of the piezoelectric body, a rear surface electrode layer that is positioned at the other side in the thickness direction of the piezoelectric body, and an interlock conductive portion that interlocks the surface electrode layer and the rear surface electrode layer to each other.

3. The ultrasound transducer according to claim 2, wherein the first terminal is connected to the rear surface electrode layer of the first electrode between the piezoelectric element and the support main body portion.

4. The ultrasound transducer according to claim 1, wherein the second terminal is connected to the second electrode between the piezoelectric element and the support main body portion.

5. The ultrasound transducer according to claim 1, wherein the piezoelectric element includes a first portion and a second portion, the first portion of the piezoelectric element including a portion overlapping the first terminal and a portion overlapping the second terminal, in the thickness direction, and the second portion of the piezoelectric element including an entirety of a region at the other side in the thickness direction of the second portion, which is covered by the support main body portion.

6. The ultrasound transducer according to claim 5, wherein an outer periphery of the piezoelectric element is square.

7. The ultrasound transducer according to claim 5, wherein the first and second portion of the piezoelectric element each include an area, and wherein the area in the second portion of the piezoelectric element is larger than the area in the first portion of the piezoelectric element.

8. The ultrasound transducer according to claim 5, further comprising:

an acoustic matching member, the acoustic matching member covering at least a part of a surface side of second portion of the piezoelectric element.

9. A diagnostic imaging apparatus, the diagnostic imaging apparatus comprising:

a diagnostic imaging catheter, the diagnostic imaging catheter including an insertion portion and an operation portion, the insertion portion includes an ultrasound probe and a sheath, the ultrasound probe including the ultrasound transducer of claim 1; and an external device configured to be mechanically and electrically connected to the diagnostic imaging catheter through a hub, and wherein the electric signal lines of the ultrasound probe extend from the ultrasound probe to a connector portion of the hub, and wherein the connector portion of the hub is configured to electrically connect the ultrasound probe and the external device to each other.

10. The diagnostic imaging apparatus according to claim 9, wherein the first electrode of the piezoelectric element includes a surface electrode layer that is positioned at the one side in the thickness direction of the piezoelectric body, a rear surface electrode layer that is positioned at the other side in the thickness direction of the piezoelectric body, and an interlock conductive portion that interlocks the surface electrode layer and the rear surface electrode layer to each other.

11. The diagnostic imaging apparatus according to claim 10, wherein the first terminal is connected to the rear surface electrode layer of the first electrode between the piezoelectric element and the support main body portion.

12. The diagnostic imaging apparatus according to claim 10, wherein the second terminal is connected to the second electrode between the piezoelectric element and the support main body portion.

13. The diagnostic imaging apparatus according to claim 10, wherein the piezoelectric element includes a first portion including a portion overlapping the first terminal and a portion overlapping the second terminal, in the thickness direction, and a second portion excluding the first portion, and an entirety of a region at the other side in the thickness direction of the second portion is covered by the support main body portion.

14. The ultrasound transducer according to claim 1, wherein the support main body portion of the support member covers an entirety of a surface of the piezoelectric body of the piezoelectric element.

15. The ultrasound transducer according to claim 1, wherein the pair of grooves in a transverse cross section to the direction orthogonal to the thickness direction each have a rectangular shape.

16. The ultrasound transducer according to claim 1, wherein the pair of grooves in a transverse cross section to the direction orthogonal to the thickness direction each have a V-character shape.

17. The ultrasound transducer according to claim 1, wherein the pair of grooves in a transverse cross section to the direction orthogonal to the thickness direction each have a circular shape.

* * * * *